US008998955B2

(12) United States Patent
Calvosa et al.

(10) Patent No.: US 8,998,955 B2
(45) Date of Patent: Apr. 7, 2015

(54) INTERSPINOUS VERTEBRAL DISTRACTOR FOR PERCUTANEOUS IMPLANTATION

(75) Inventors: Giuseppe Calvosa, Pisa (IT); Raphael Bartalesi, Florence (IT); Miria Tenucci, Lucca (IT)

(73) Assignee: Giuseppe Calvosa (IT)

( * ) Notice: Subject to any disclaimer, the term of this patent is extended or adjusted under 35 U.S.C. 154(b) by 442 days.

(21) Appl. No.: 12/865,856

(22) PCT Filed: May 28, 2008

(86) PCT No.: PCT/IB2008/001344
§ 371 (c)(1),
(2), (4) Date: Nov. 1, 2010

(87) PCT Pub. No.: WO2009/098536
PCT Pub. Date: Aug. 13, 2009

(65) Prior Publication Data
US 2011/0046674 A1 Feb. 24, 2011

(30) Foreign Application Priority Data

Feb. 7, 2008 (IT) ................. PI2008A0010

(51) Int. Cl.
*A61B 17/70* (2006.01)
(52) U.S. Cl.
CPC ......... *A61B 17/7065* (2013.01); *A61B 17/7053* (2013.01)
(58) Field of Classification Search
CPC ................................................. A61B 17/7065
USPC .................. 606/249, 257, 259, 261, 263, 276
See application file for complete search history.

(56) References Cited

U.S. PATENT DOCUMENTS

| 7,959,652 B2 * | 6/2011 | Zucherman et al. .......... 606/249 |
| 8,123,782 B2 * | 2/2012 | Altarac et al. ............... 606/249 |
| 2006/0084985 A1 * | 4/2006 | Kim .............................. 606/61 |

(Continued)

FOREIGN PATENT DOCUMENTS

| GB | 2436292 | 9/2007 |
| WO | 2006/102269 | 9/2006 |

(Continued)

OTHER PUBLICATIONS

PCT Written Opinion mailed on Dec. 17, 2008 for PCT Application No. PCT/IB2008/001344 filed May 28, 2008 in the name of Giuseppe Calvosa.

(Continued)

*Primary Examiner* — Ellen C Hammond
*Assistant Examiner* — Stuart S Bray
(74) *Attorney, Agent, or Firm* — Steinfl & Bruno LLP

(57) ABSTRACT

Interspinous distractor for percutaneous implantation comprising a central body (10) and two couples of stabilizears (14*a*, 14*b*; 14*c*, 14*d*), hinged at the end of the body (10) in order to rotate from a closed position, which assists the percutaneous implantation of the distractor, to a spread apart position, which limits its movement stabilizing it in the interspinous gap. Means are provided for causing the rotation of the stabilizears that can be operated percutaneously, in particular, by means of cam shaped elements sliding axially and adapted to engage a cam-shaped surface, or by a system of tie members, and special tools. With respect to the known distractors it can implanted end extracted percutaneously and in a much easier way.

19 Claims, 19 Drawing Sheets

(56) References Cited

U.S. PATENT DOCUMENTS

| | | | |
|---|---|---|---|
| 2006/0264938 A1* | 11/2006 | Zucherman et al. | 606/61 |
| 2006/0271049 A1* | 11/2006 | Zucherman et al. | 606/61 |
| 2007/0010813 A1* | 1/2007 | Zucherman et al. | 606/61 |
| 2007/0032790 A1* | 2/2007 | Aschmann et al. | 606/61 |
| 2007/0161991 A1* | 7/2007 | Altarac et al. | 606/61 |
| 2007/0173832 A1* | 7/2007 | Tebbe et al. | 606/61 |
| 2007/0225807 A1* | 9/2007 | Phan et al. | 623/17.11 |
| 2007/0260245 A1* | 11/2007 | Malandain et al. | 606/61 |
| 2007/0276370 A1* | 11/2007 | Altarac et al. | 606/61 |
| 2008/0108990 A1* | 5/2008 | Mitchell et al. | 606/61 |
| 2008/0177391 A1* | 7/2008 | Mitchell et al. | 623/17.16 |
| 2008/0195152 A1* | 8/2008 | Altarac et al. | 606/249 |
| 2008/0287997 A1* | 11/2008 | Altarac et al. | 606/249 |
| 2008/0294263 A1* | 11/2008 | Altarac et al. | 623/17.16 |
| 2008/0319550 A1* | 12/2008 | Altarac et al. | 623/17.16 |
| 2009/0138045 A1* | 5/2009 | Ciupik et al. | 606/249 |
| 2009/0138046 A1* | 5/2009 | Altarac et al. | 606/249 |
| 2009/0138055 A1* | 5/2009 | Altarac et al. | 606/86 A |
| 2009/0222043 A1* | 9/2009 | Altarac et al. | 606/249 |
| 2009/0234389 A1* | 9/2009 | Chuang et al. | 606/249 |
| 2009/0292316 A1* | 11/2009 | Hess | 606/249 |
| 2010/0057130 A1* | 3/2010 | Yue | 606/249 |
| 2010/0106191 A1* | 4/2010 | Yue et al. | 606/249 |
| 2010/0174373 A1* | 7/2010 | Galley et al. | 623/17.13 |
| 2011/0077686 A1* | 3/2011 | Mishra et al. | 606/249 |
| 2011/0160773 A1* | 6/2011 | Aschmann et al. | 606/249 |
| 2012/0029565 A1* | 2/2012 | Seifert et al. | 606/249 |
| 2012/0143341 A1* | 6/2012 | Zipnick | 623/17.16 |
| 2013/0325067 A1* | 12/2013 | Calvosa et al. | 606/249 |
| 2013/0331890 A1* | 12/2013 | Calvosa et al. | 606/249 |

FOREIGN PATENT DOCUMENTS

| | | |
|---|---|---|
| WO | 2007/075788 | 7/2007 |
| WO | 2007/111979 | 10/2007 |
| WO | 2008/057838 | 5/2008 |
| WO | 2009/098536 | 8/2009 |

OTHER PUBLICATIONS

PCT International Search Report mailed on Aug. 23, 2011 for PCT/IB2010/055379 filed on Nov. 23, 2010 in the name of Giuseppe Calvosa.

PCT Written Opinion mailed on Aug. 23, 2011 for PCT/IB2010/055379 filed on Nov. 23, 2010 in the name of Giuseppe Calvosa.

PCT International Search Report mailed on Aug. 23, 2011 for PCT/IB2010/055377 filed on Nov. 23, 2010 in the name of Giuseppe Calvosa.

PCT Written Opinion mailed on Aug. 23, 2011 for PCT/IB2010/055377 filed on Nov. 23, 2010 in the name of Giuseppe Calvosa.

PCT International Search Report for PCT/IB2008/001344filed on Dec. 9, 2008 in the name of Giuseppe Calvosa, et al.

* cited by examiner

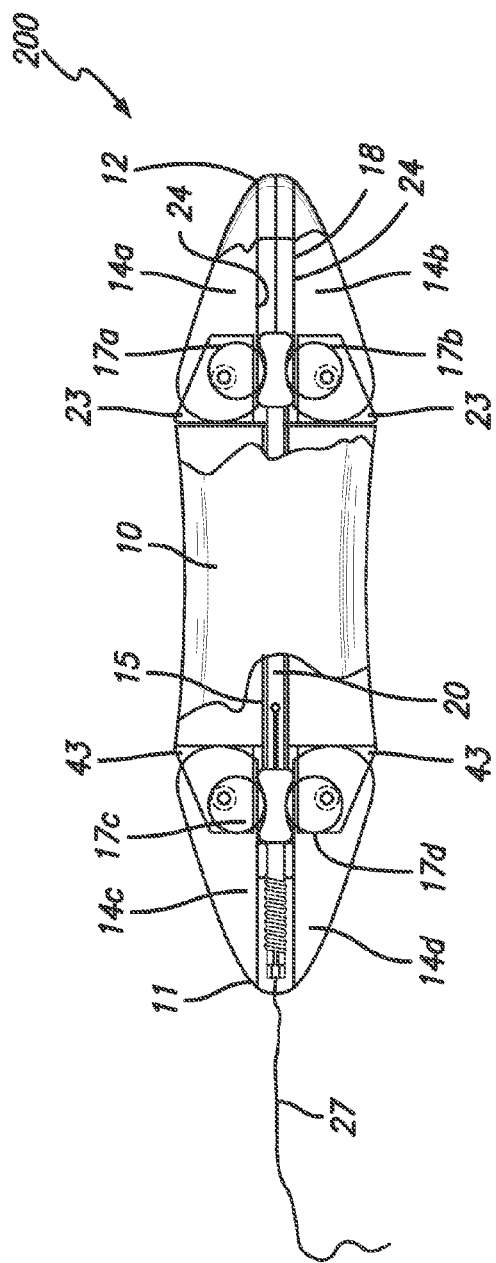
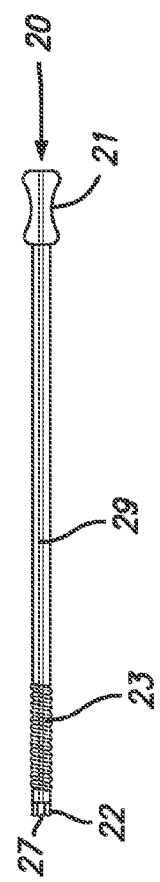
FIG. 2A
FIG. 2B

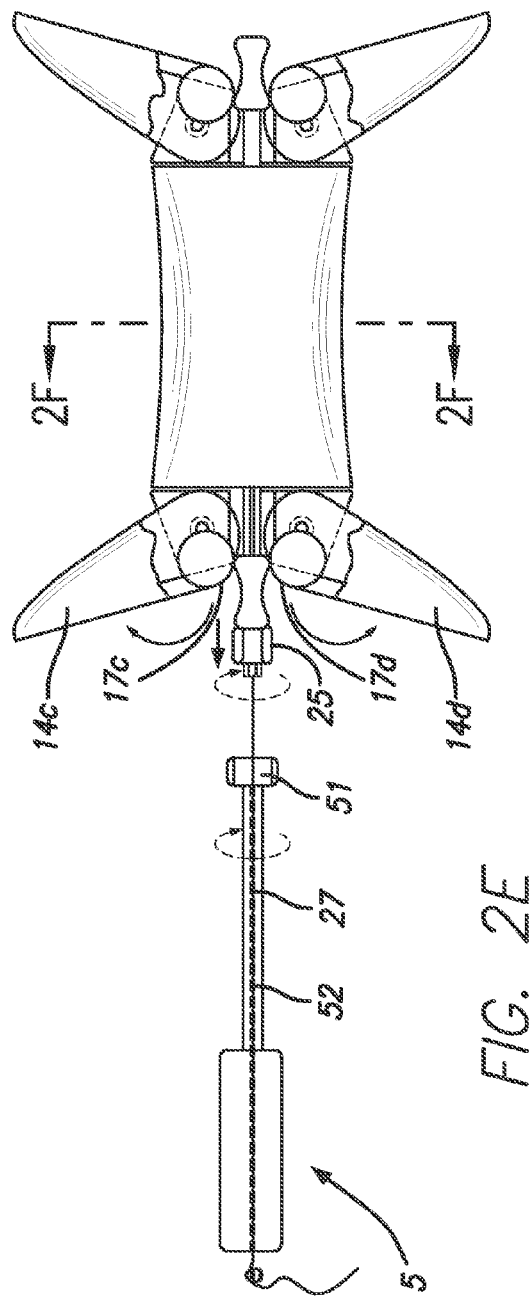
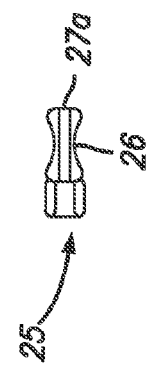
FIG. 2G
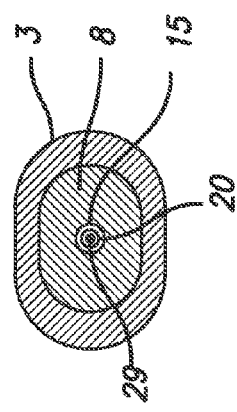
FIG. 2F
FIG. 2E

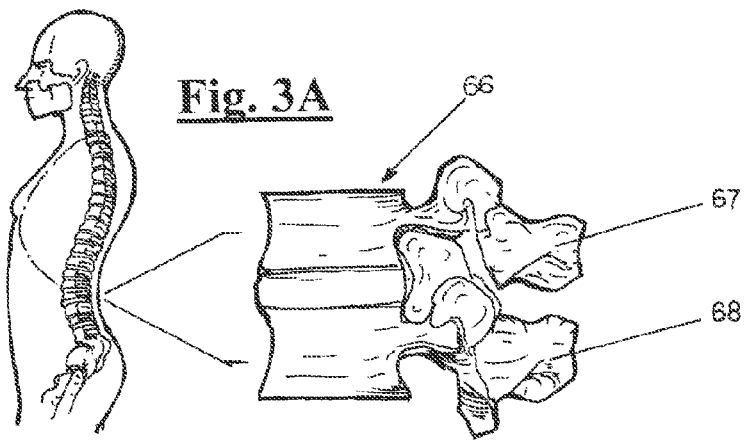
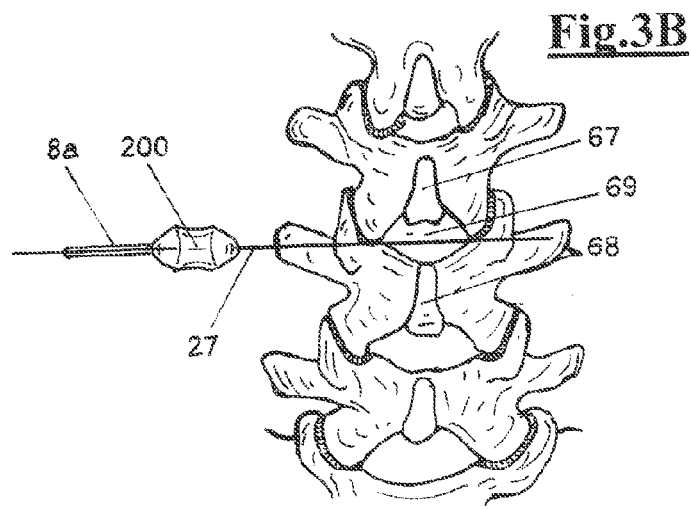
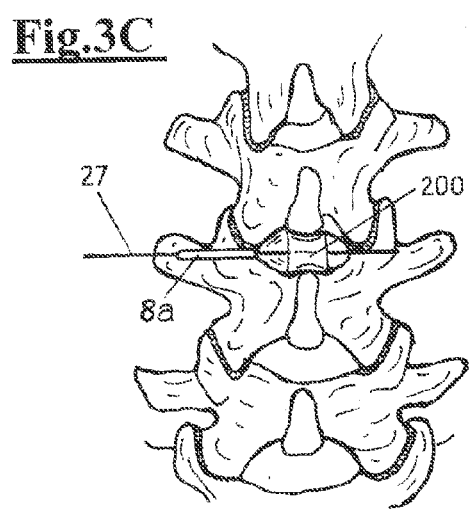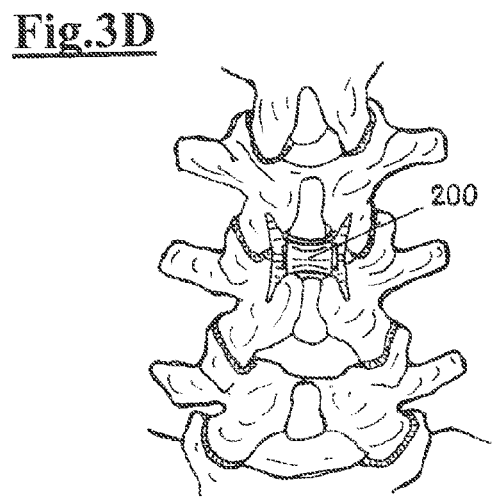

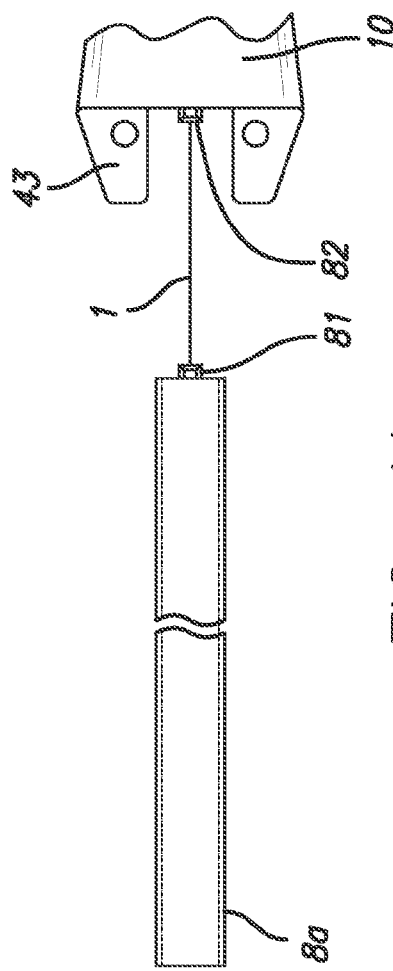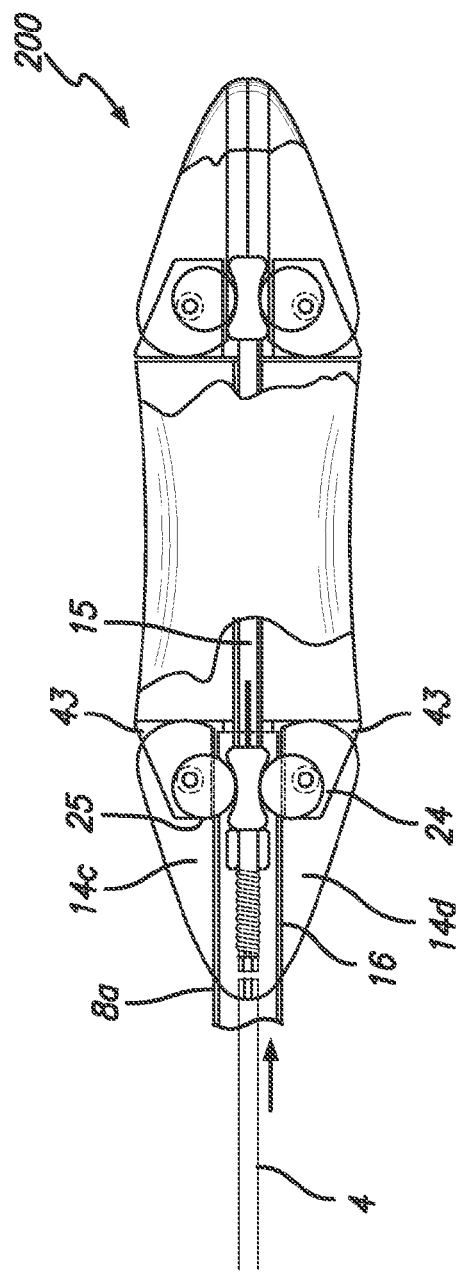

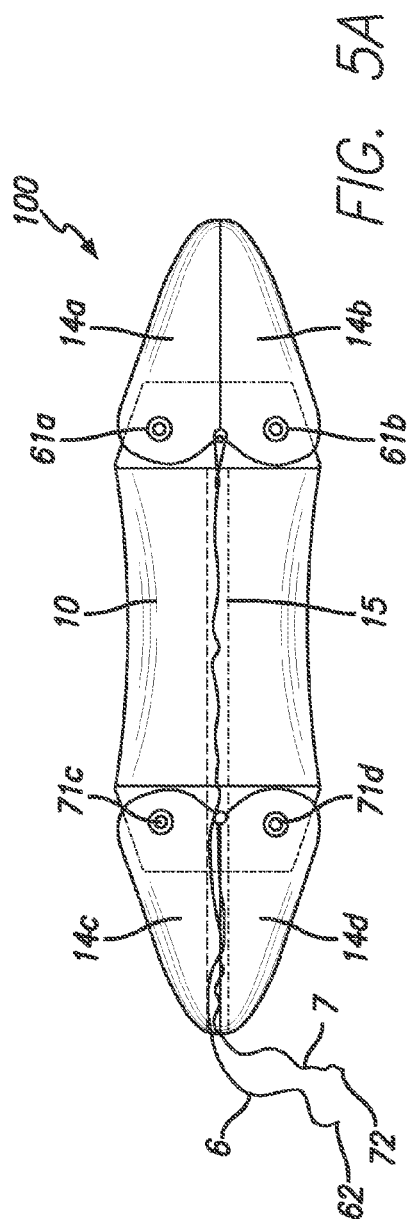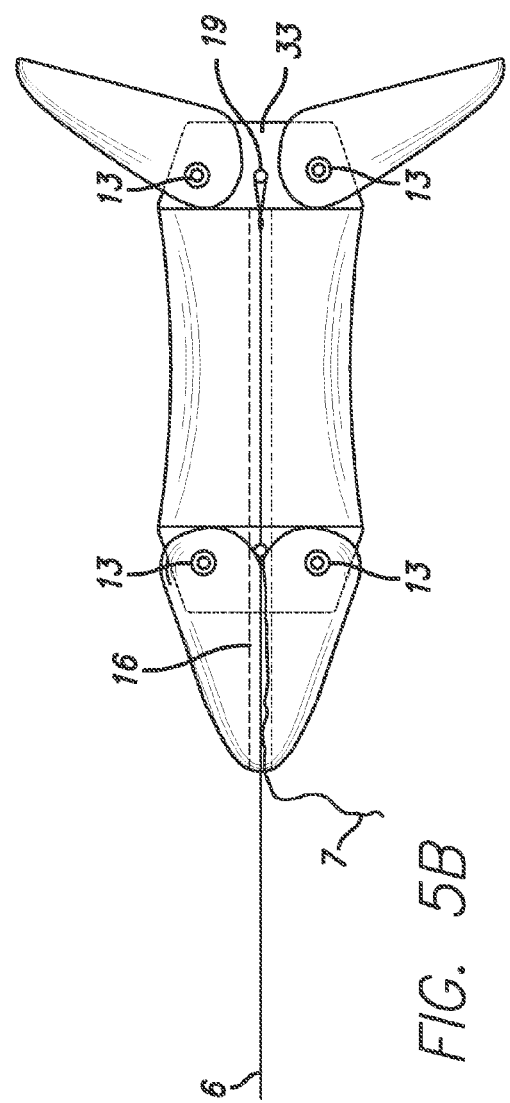

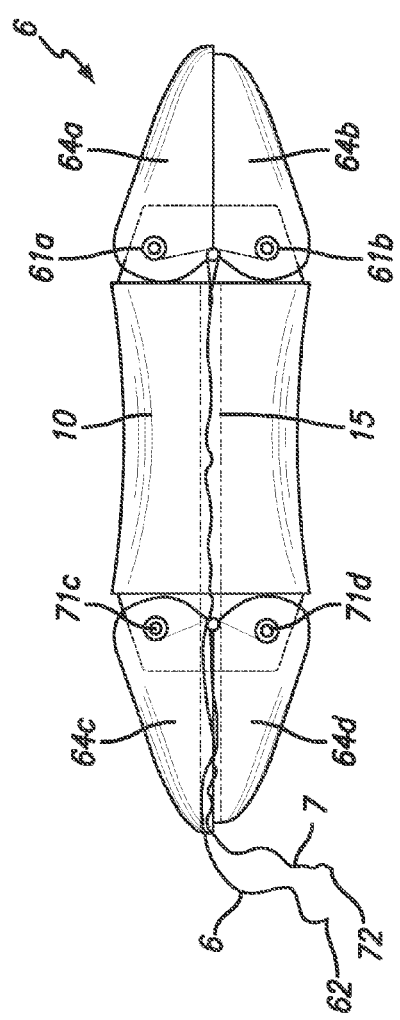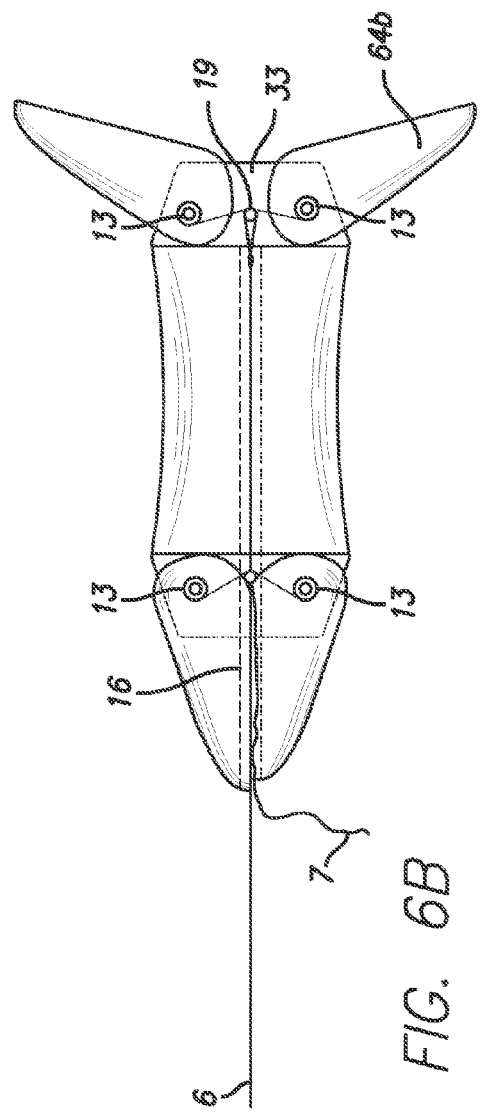
FIG. 6A
FIG. 6B

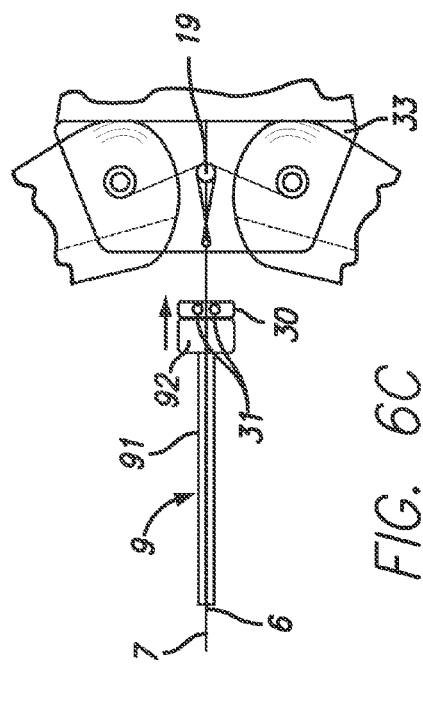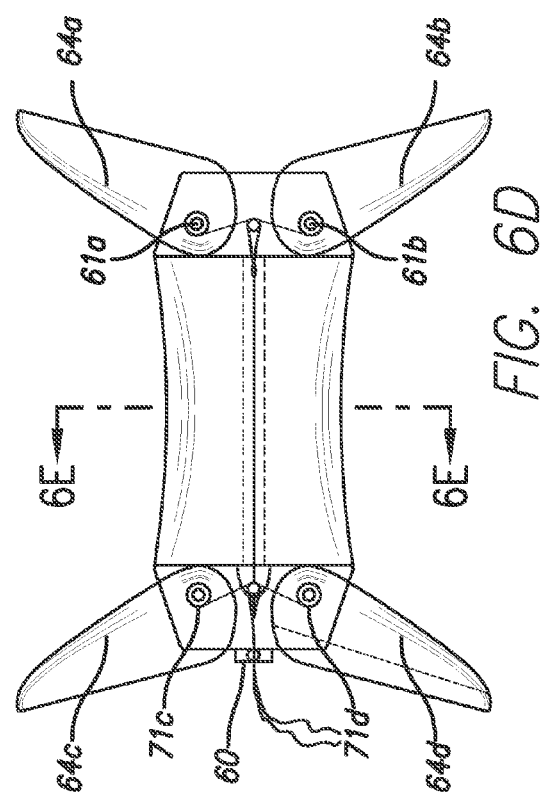

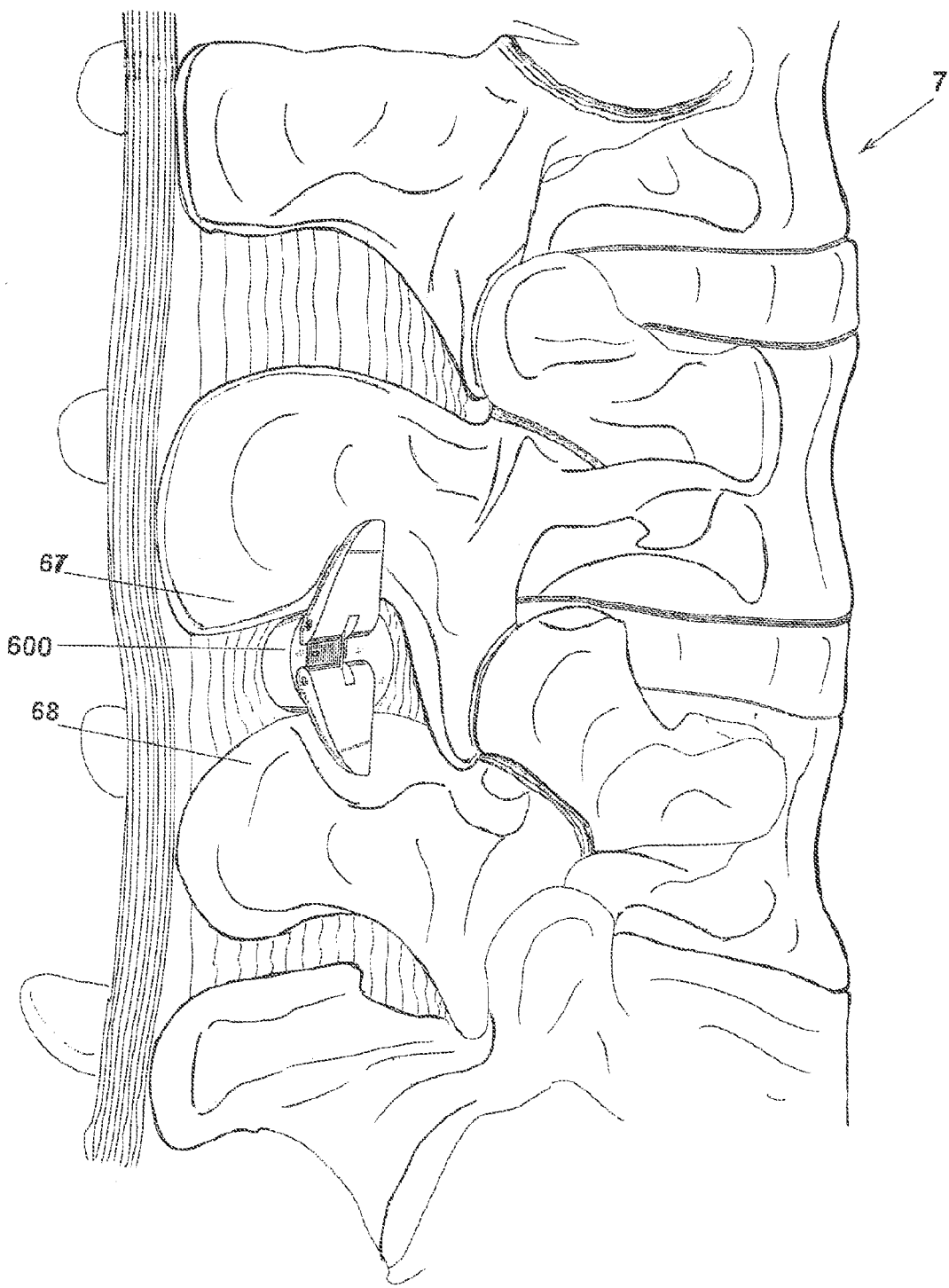

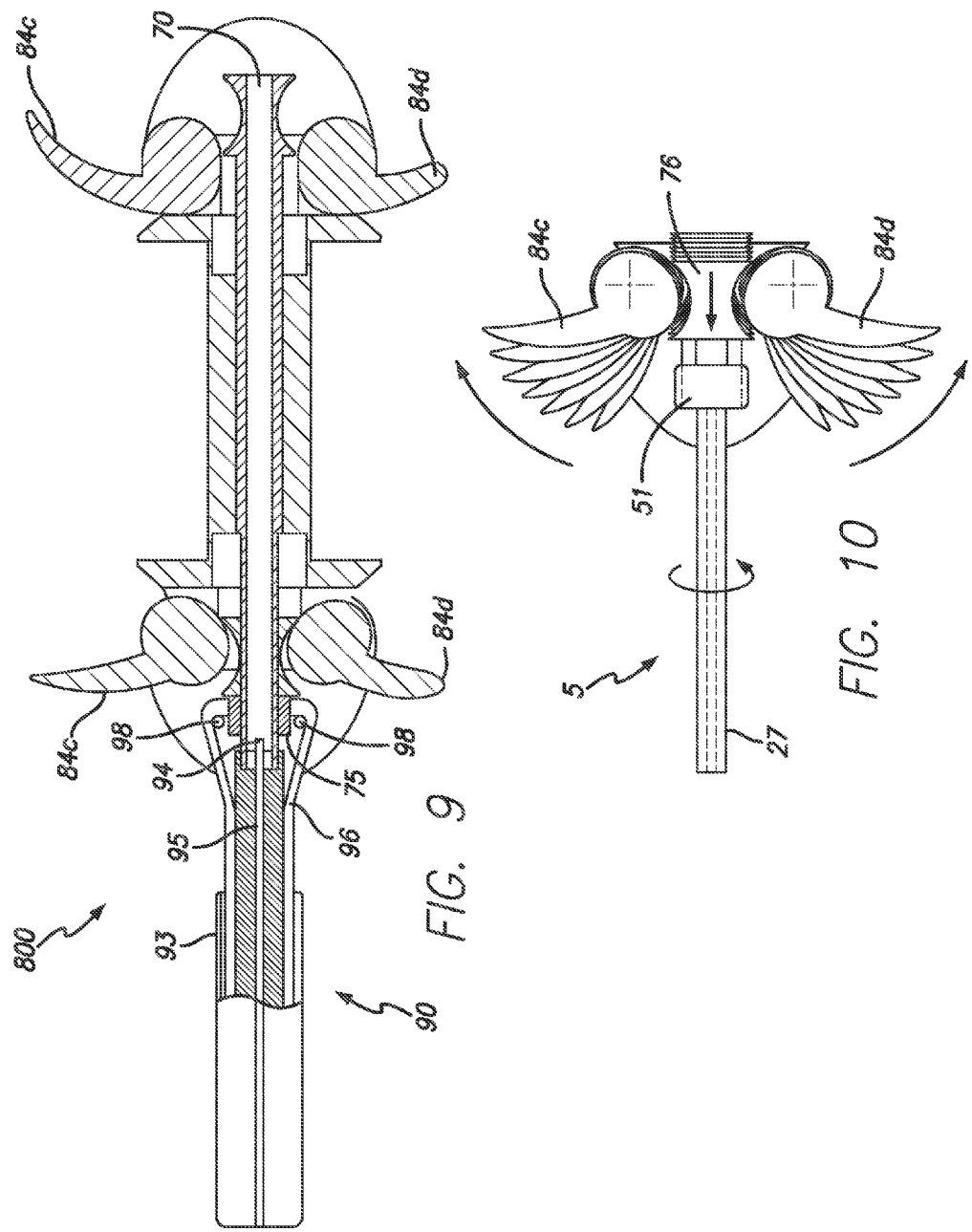

INTERSPINOUS VERTEBRAL DISTRACTOR FOR PERCUTANEOUS IMPLANTATION

CROSS REFERENCE TO RELATED APPLICATIONS

The present application is the US national stage of International Application PCT/IB2008/001344 filed on May 28, 2008 which, in turn, claims priority to Italian Application PI2008A000010, filed on Feb. 7, 2008.

FIELD

The present invention relates to an interspinous vertebral distractor adapted to percutaneous implantation from a right or left direction with respect to the interspinous gap.

BACKGROUND

Intervertebral distractors are devices adapted to space two adjacent vertebrae. In particular, the distractors according to the present invention are prostheses for steady implantation in the space set between the spinous processes of two adjacent vertebrae, in order to maintain an intervertebral distraction adapted to limit the loads transmitted between the vertebrae in case of degenerative diseases of the intervertebral disc, thus limiting the associated painful effects.

With respect to other vertebral prostheses, interspinous distractors can be easily implanted, in view of the relative simplicity according to which the spinous processes of two adjacent vertebrae can be slightly spread apart. For the same reasons, such distractors do not jeopardize the local mobility of the spine when bending, and reduce hyperextension. Notwithstanding such advantages, known stabilization problems exist. In other words, an interspinous distractor has to be kept in position, in particular it has to be constrained with respect to movements, thus affecting its functionality or causing it to exit from the interspinous gap, with movements in a plane orthogonal to the spine.

In particular, WO2006102269 describes interspinous distractors for keeping the implant within the interspinous gap, comprising a central portion adapted to be contained in the interspinous gap providing an interspinous support adapted to maintain a desired distraction, and stop members consisting of two ends portions, one of which is fixed while the other is moveable, the latter comprising elements movable according to two extreme positions. The fixed end has a profile and a size such that it can be approached laterally against the spinous processes of the two adjacent vertebrae. Adjusting means are provided for the moveable end, on which the surgeon acts once the device is implanted, thus forming a bilateral limitation to sliding for the distractor according to its own longitudinal axis. The interspinous and the supraspinous ligament assist settling of the implant between the spinous processes, in particular with respect to movements in a plane orthogonal to the spine, thus ensuring a local mobility of the spine.

However, such device cannot be implanted percutaneously, in view of an excessive size of the fixed portion of the stop members, which influences the overall size of the distractor, and also because the means for adjusting the movable part of the stop members cannot be operated percutaneously.

A further device is also known, called Synthes®, comprising a central body with a substantially cylindrical shape and two couples of movable and reversible stop members that project from the central body, such that the radial size of the device, in a closed position, does not exceed the substantially cylindrical body. Once the body has been endoscopically placed between the spinous processes, the surgeon acts always percutaneously on position adjusting elements of such mobile stop members, causing them to partially exit from the body through suitable slits, the stop members being conformed to hook the spinous processes. Even in this case, the interspinous ligament assists placement of the prosthesis between the spinous processes. The mobile stop members, however, being housed in the cylindrical body, have to rotate in order to protrude from the respective slit. This entails a high internal mechanical complexity. Furthermore, the stop members have a portion remaining in the cylindrical body that is large enough to support the part protruding from the body, in order to assure enough blocking force to the distractor. The presence of the stop members and of the relative mechanisms in the cylindrical body does not allow having distractors under a certain size.

Examples of interspinous distractors, particularly devised for cervical vertebrae, are disclosed in US20060271049A1, US2007010813A1 and in US US2008108990A1. These distractors have a body from which a wing extends, which wing can move from a closed position, not exceeding the height of the body, to a spread apart position protruding laterally with respect to the body, and can then keep the body settled between two spinous processes, in order to carry out distraction and at the same time blocking an accidental movement of the body.

SUMMARY

It is therefore a feature of the present invention to provide an intervertebral interspinous distractor that comprises effective stop members of the body within the interspinous gap and at the same time allows a percutaneous implantation.

A further feature of the present invention provides an intervertebral interspinous distractor that can be blocked in a steady position from both body ends without introducing locking elements fixed from the outside.

A further feature of the present invention provides an intervertebral interspinous distractor, adapted to be percutaneously implanted, which is of much easier construction than prior art distractors, in particular with reference to the stop members.

Yet another feature of the present invention provides an intervertebral interspinous distractor, adapted to be percutaneously implanted, in particular for vertebrae of the lumbar-sacral zone of the spine.

A further feature of the present invention provides an intervertebral interspinous distractor, adapted to be percutaneously implanted, which has a small size, particularly adapted to introduction in interspinous spaces different from the lumbar region and to treat patients of low size, typically children.

It is also a feature of the present invention to provide an interspinous distractor, adapted to be percutaneously implanted and extracted, with relevant advantages for patients where the distractor is temporarily mounted in case of disc compressions awaiting permanent treatment.

A further feature of the present invention provides an intervertebral interspinous distractor, in particular for introduction between spinous processes of lumbar vertebrae, where the loads necessary for distraction are the highest.

Still another feature of the present invention provides an interspinous distractor which allows, without substantial structural changes, an implantation both in young patients and in elder patients, and for different degrees of disc degeneration.

Still another feature of the present invention provides an interspinous distractor adapted to be implanted in patients suffering from scoliosis or other deformations of the spine.

These and other features are achieved by an interspinous implant comprising:

an elongated body with a first and a second end and a predetermined transversal dimension, adapted to provide an interspinous support between two adjacent spinous processes, the body having a longitudinal axis;

a first and a second couple of mobile stabilizers, respectively connected to the first and second ends of the elongated body, the stabilizers being adapted to rotate from a closed position, in which they form a pointed extension of the elongated body, assisting a percutaneous implantation of the distractor, and a spread apart position, wherein the stabilizers in use limit the movement of the distractor, providing a barrier adapted to contain between them the spinous processes;

means that can be operated percutaneously movable along the axis and associated with the elongated body and the stabilizers, for bringing the stabilizers from the closed position to the spread apart position or vice versa, the stabilizers being connected to the ends at pivot points distant from the axis, the stabilizers having with respect to the body a distal end and a proximal end, such that the means that can be operated percutaneously moving along the axis acts on the stabilizers for causing both the first and the second couple of stabilizers to rotate about the pivot points so that the distal end moves from the closed position to the spread apart position and the proximal end is kept closed to the axis.

The ability of adjusting percutaneously the position of the two stabilizers, from a closed introduction position to a spread apart stabilization position, allows at the same time to implant easily the device and to settle it in the interspinous gap, by mini-invasive implantation steps.

In particular, the position of the stabilizers can be changed with continuity, avoiding lateral backlash of the distractor without forcing too much the stabilizers against the spinous processes. Furthermore, it is possible to ensure that the stabilizers achieve a blocking position, since the stabilizers can be blocked in any desired position.

Advantageously, the means that can be operated percutaneously cause a non-simultaneous opening movement of the stabilizers with respect to the spinous processes in the approaching direction, with advantages for operators as they need not use imaging systems, for example with sonographic probes, for checking the relative position of the implant with respect to the spinous processes. In particular, it is possible to first open the distal stabilizers with respect to the hands of the surgeon, then causing them to touch the spinous processes in such spread apart position with a backward movement, and then opening the proximal stabilizers. Furthermore, this opening sequence allows to easily carry out distraction in presence of angular deformity, scoliosis, ossified tissues on the spinous processes that normally hamper introduction with known systems.

In a particular advantageous exemplary embodiment, at least one couple of the stabilizers can rotate about the pivot point beyond the spread apart position continuing further for angles larger than 90°, in particular, between 120° and 180°. In this way, a percutaneous extraction is permitted, preventing the ends of the stabilizers from blocking the extraction. In particular, the two stabilizers that can rotate about the pivot point beyond the spread apart position continuing further for angles larger than 90° have a curved shape with a concavity oriented opposite the axis of the body during introduction, and towards the axis of the body during extraction.

Advantageously, the elongated body has substantially elliptical transversal sections wherein, in use, a longer axis lies in a plane substantially orthogonal to the spine.

Furthermore, the elongated body can have a conical shape, preferably with a cone angle of 4-5°, which can be advantageously used in treating scoliosis. In this case, the larger diameter of the frustoconical is arranged on the side of the concavity of the deformity of the spine.

Advantageously, the interspinous distractor has a first and a second lateral stabilizers that are arranged, in use, below the median horizontal plane of the body of the distractor, and that are shorter than corresponding third and fourth stabilizers arranged, in use, above the median plane. In this way, interferences with the vertebra just below the two distracted vertebrae are prevented, for example in presence of scoliosis or other vertebral degenerations.

Furthermore, advantageously, each lateral stabilizer is asymmetrical in a vertical plane. In this way, a possible interference with the lateral processes of the adjacent vertebrae of the spine is avoided.

Advantageously, the stabilizers are enclosed laterally between fixed protection shells. In this way, a "torpedo-like" profile of the distractor is obtained, which is of assistance during a percutaneous implantation and extraction.

The means that can be operated percutaneously, in a first exemplary embodiment, comprises a rod slidingly arranged in a longitudinal recess of the elongated body, the rod having at one end a cam-shaped portion adapted to be put in a space comprised within the stabilizers of the first couple, such stabilizers each having a cam-shaped surface at the proximal end with respect to the body, adapted to engage with a cam-shaped portion of the rod so that a translation of the rod causes a rotation of the lateral stabilizers.

In particular, the proximal end has a convex shape, and the cam-shaped portion of the rod has a corresponding concave shape, whereby the convex shape and concave shape form two conjugate profiles.

Alternatively, the conjugate profiles of the proximal end and of the cam-shaped portion of the rod are convex, and have on the surface gear-like portions.

Advantageously, the rod has a gripping end opposite to the cam-shaped portion, and this gripping end is adapted to be maneuvered percutaneously with a first tool.

Preferably, the gripping end is adapted to engage with a spanner-like portion of the tool, this gripping end being selected from the group comprised of a female end for a respective male spanner-like portion, and a male end for a respective female spanner-like portion.

Advantageously, the means that can be operated percutaneously comprises a cam-shaped element adapted to be housed in a space comprised within the stabilizers of the second couple and to be maneuvered with a second tool, and the cam-shaped element is engageable and lockable on a portion of the rod opposite to the cam-shaped portion, in order to cause a rotation of the stabilizers of the second couple from the closed position to the spread apart position.

In particular, the portion of the rod opposite to the cam-shaped portion has a threaded portion and the cam-shaped element is a cam-shaped nut adapted to be screwed on the threaded portion to cause a rotation of the stabilizers of the second couple from the closed position to the spread apart position or vice-versa.

Preferably, the second tool has a spanner-like portion adapted to engage with the cam-shaped nut.

Advantageously, the intervertebral distractor comprises means for guiding the cam-shaped element and the tool towards the distraction body arranged in an intervertebral interspinous gap.

In particular, the means for guiding can comprise a wire, and the rod has an axial hole from which the wire extends, whereby the cam-shaped element and the tool are guided along the axis of the rod by the wire.

Preferably, the axial hole of the rod is a through hole and the wire is adapted to guide the prosthesis towards the interspinous gap. In particular, it is possible to use a K wire, known also as Kirschner wire, which, as well known, is sufficiently stiff for such use.

Advantageously, a tubular guide is provided having at the end means for releasably engaging the intervertebral distractor, the tool being in use guided towards the gripping end of the rod and towards the nut through the tubular guide.

Preferably, the engagement means between distractor and tubular guide comprises a couple of teeth arranged at one end of the tubular guide, adapted to engage with corresponding holes provided in the distractor.

Advantageously, in order to percutanously extract the intervertebral distractor, a tool is provided; the tool is adapted to engage with the head of the screw for rotating it. The tool is further associated with a device adapted to keep the nut still. In particular, the device adapted to keep the nut still has a plurality of arms telescopically protruding from the tool adapted to engage with the head of the screw, the plurality of arms being suitable to form a gripper that grips the head of the screw.

In a second exemplary embodiment of the invention, the means that can be operated percutaneously comprises: a flexible tie member fixed to the stabilizers of at least one of the couples of stabilizers, so that such stabilizers are brought from the closed position to the spread apart position by pulling the tie member, and means for blocking the flexible tie member when the stabilizers have achieved the spread apart position.

Advantageously, the means for blocking the flexible tie member are reversible, in order to be released for bringing the stabilizers from the actual spread apart position to the closed position for extracting the implant.

In particular, the means for blocking the flexible tie member comprises a couple of counter-rotating friction wheels or circular sectors arranged about respective axes substantially perpendicular to a direction defined by the stretched flexible tie member, such wheels or circular sectors being such that they keep an interference position due to the mutual friction exerted and with the flexible tie member arranged between them.

As apparent from the above, and as much clearer from the description of the preferred exemplary embodiments, the stop members have limited mechanical complexity and are easy to manufacture, improving the distractors of the prior art.

The distractor according to the invention may have a nominal size selected from the group comprised of: 8, 10, 12, 14 mm, thus being adapted to a percutaneous implantation.

Preferably, the elongated body and the stabilizers are made of a metal material, in particular titanium or titanium alloy. Advantageously, the elongated body and the stabilizers have an outer coating surface of a material based on a thermoplastic polymer, which is chosen according to the disc degeneration degree of the vertebra supported by the distractor. In particular, for a slight degeneration degree, in particular for second or third disc degeneration degrees according to the Pfirman classification, soft materials are more suitable, with reference to the spinous apophysis characteristics, whereas if the degeneration is much more serious (fourth or fifth disc degeneration degrees) a harder material is indicated, i.e. having a modulus of elasticity close to that of the bones concerned with the implant. In particular, the material with modulus of elasticity close to that of the bones can be selected among polyaryletherketones, known for their good biocompatibility characteristics. In particular, the polymer can be polyetheretherketone, also known commercially as PEEK®.

By way of example, softer materials, adapted to treat less serious degenerations, can be instead selected among polyurethane foams. Such coating material also assists the introduction of the distractor between the spinous processes and limits the even unlikely possibility of mechanical local overloads on the spinous processes.

BRIEF DESCRIPTION OF THE DRAWINGS

The invention will be made clearer with the following description of an exemplary but not limitative embodiment thereof, with reference to the attached drawings wherein:

FIG. 2A is an elevational partially cross-sectional side view of an interspinous distractor according to the invention, where the position of the stabilizers is changed by means of cam-shaped elements adapted to be housed in a space between the stabilizers;

FIG. 2B shows a rod present in the distractor of FIG. 2A;

FIG. 2E shows the distractor of FIG. 2A after variation of the position of the stabilizers of the second couple by means of the nut and the tool;

FIG. 2F shows the median cross sectional view F-F of the elongated body of the distractor shown in FIG. 2E;

FIG. 2G is a view of a cam-shaped nut;

FIG. 3A shows a portion of lumbar vertebrae, where the distractor can be inserted according to the invention;

FIGS. 3B-3D show the steps of introducing the distractor according to the invention;

FIG. 4A shows a tubular guide and an embracing portion thereof on the body of the distractor; —

FIGS. 4B-4C show two steps of interaction of the tubular guide with the rod, in the exemplary embodiment of FIGS. 2A-2G;

FIG. 5A is an elevational side view of an intervertebral distractor of interspinous type according to the invention, where the position of the stabilizers is changed by means of flexible tie members connected to them;

FIG. 5B shows the distractor of FIG. 5A after variation of the position of the stabilizers of the first couple by means of traction of a first flexible tie member;

FIG. 6A shows the exemplary embodiment of the distractor of FIG. 5A, where the stabilizers that are arranged in use below to a median horizontal plane of the body of the prosthesis are shorter than the stabilizers arranged, in use, above the plane;

FIG. 6B shows the distractor of FIG. 6A after variation of the position of the stabilizers of the first couple by means of traction of a first flexible tie member;

FIG. 6C shows a wire pulling member, consisting of a couple of friction wheels; —FIG. 6D shows the distractor of FIG. 6B after opening also of the stabilizers of the second couple by means of traction of a second flexible tie member, the two flexible tie members being pulled by the device shown in additional detail in FIG. 6C;

FIG. 7 shows the device of FIG. 6A-F arranged between the spinous apophysis of two adjacent vertebrae 67 and 68;

—FIG. 5B shows a rod comprised in the distractor of FIG. 8A;

FIG. 9 shows the distractor of FIG. 8 A-G and one tool for bringing the stabilizers of the second couple from the spread apart position of FIG. 8E to the backward position of FIG. 8G;

FIG. 10 shows a tool that engages the nut of FIG. 8D of the tool of FIGS. 8A-G for moving the stabilizers of the second couple from the closed position to a spread apart anatomic position, the position being chosen to give the stabilizers a desired opening angle;

DETAILED DESCRIPTION

Figure 1A:
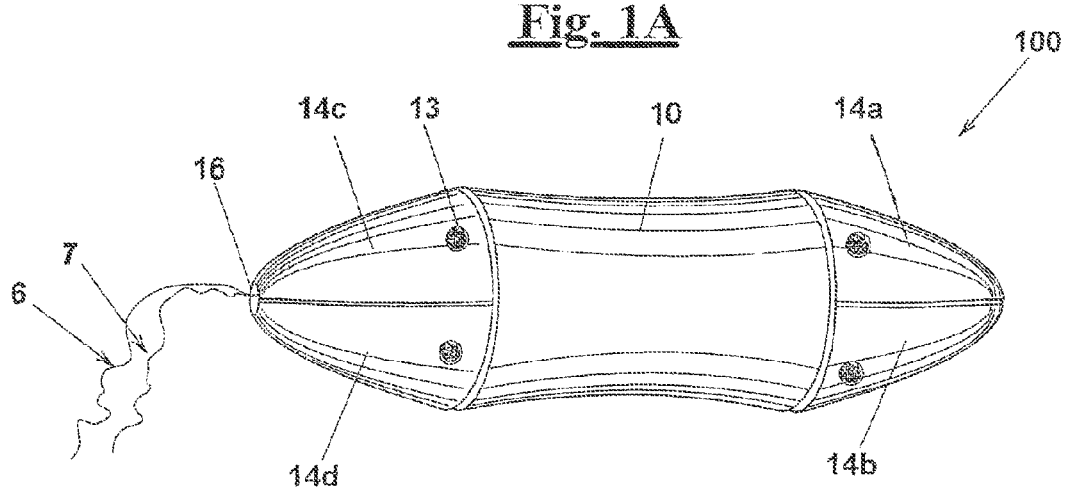
FIG. 1A is a perspective view of a first interspinous distractor according to the invention, where the stabilizers of both couples of stabilizers are in closed position.
Figure 1B:
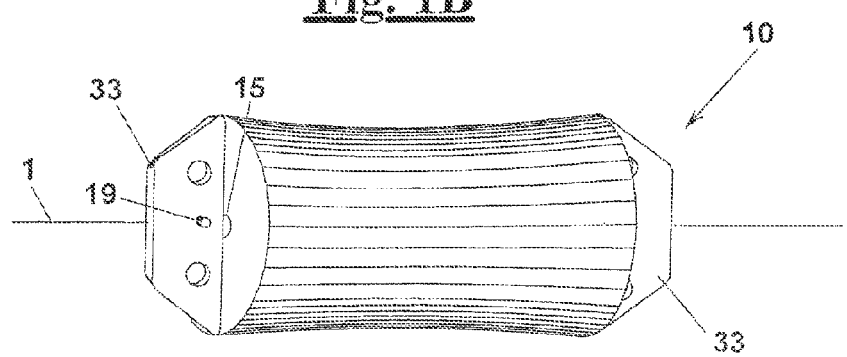
FIG. 1B is a perspective view of an elongated body comprised in the distractor of FIG. 1A.

With reference to FIGS. 1A and 1B, a first interspinous vertebral distractor 100 is described, comprising an elongated body 10 and two ends 11 and 12 at which two couples of stabilizers 14a-b and 14c-d are connected by two supports 33 and two couples of hinges 13. Each stabilizer 14a-d has internally a slot that houses a portion of the corresponding support 33, shaped such that it allows a rotation about the corresponding hinge 13. In particular, the hinges 13 are distant from the longitudinal axis 1 and each stabilizer 14a-d has with respect to body 10, a distal end and a proximal end. In this way, it is possible to insert the implant percutaneously, in the way hereinafter described in the various exemplary embodiments, with a movement along the axis 1, acting on the proximal end for causing stabilizers 14a-b and 14c-d to rotate about the pivot points 13.

In FIG. 1A, distractor 100 is shown with both couples of stabilizers 14a-b and 14c-d in closed position, in which configuration distractor 100 is ready for a percutaneous implantation within the spinous processes of two adjacent vertebrae. FIG. 1B shows instead the elongated body 10 of the distractor alone.

A second embodiment of an interspinous distractor 800, shown in FIG. 1C, has still an elongated body 10 similar to the elongated body of distractor 100, whereas each couple of stabilizers 84a-b and 84c-d is enclosed between two fixed shells 49; furthermore, stabilizers 84a and 84b, in open position, have a convex face oriented opposite to body 10; in particular, stabilizers 84b and 84d, that are arranged in use below a plane perpendicular to the spine, are shorter than stabilizers 84a and 84d, as described hereinafter.

Figure 2C:
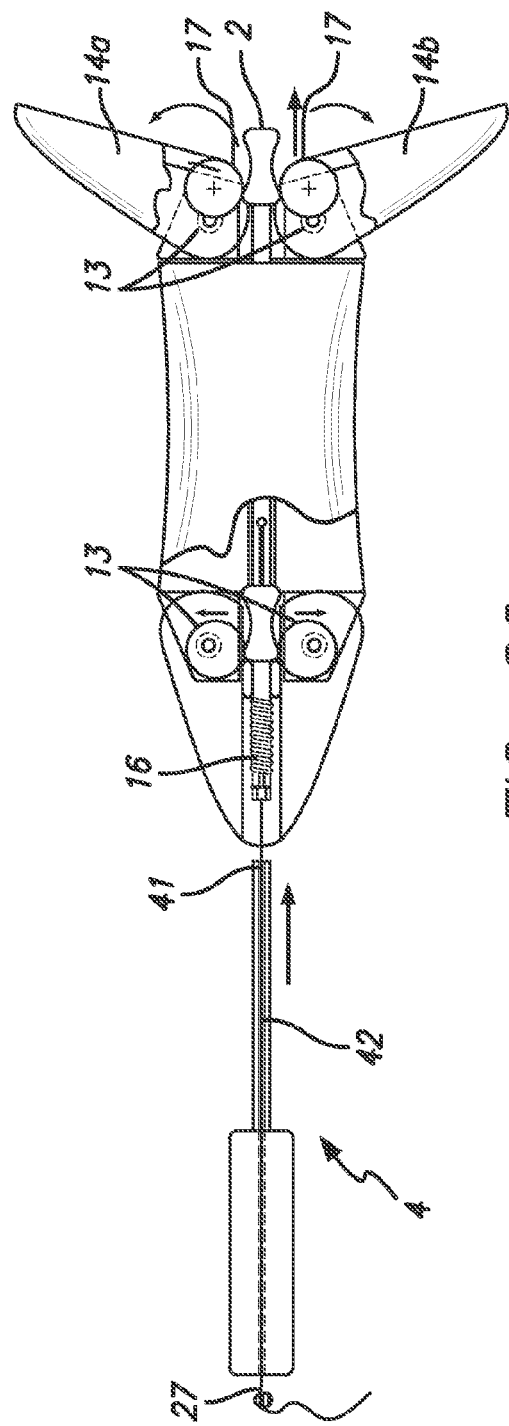
FIG. 2C shows the distractor of FIG. 2A after variation of the position of the stabilizers of the first couple by means of a tool.

FIGS. 2A-2G show an exemplary embodiment of the distractor indicated as 200, in which a rod 20 is present, the rod being able to slide in a longitudinal recess 15 of elongated body 10, having transversal sections substantially homothetic to the median cross section shown in FIG. 2F. At one end of the rod 20, shown in detail in FIG. 2B, a cam-shaped portion 21 is visible, adapted to engage with the eccentric or cam-shaped surfaces 17a-b of stabilizers 14a-b, causing a rotation thereof. The opposite end 22 is instead configured to be maneuvered with a tool 4, for example with a hexagonal head 41, or a screw driver end. During this translation, rod 20 engages also the recesses 16 and 18, which are formed respectively between the two stabilizers 14c-d and 14a-b.

By way of this maneuver, rod 20 can translate from the actual position shown in FIG. 2A to the position shown in FIG. 2C, and stabilizers 14a-b rotate about portions 43 running from the closed position to the spread apart position, whereas stabilizers 14c-d remain still in closed position. This is advantageous in use since a surgeon can choose a second moment for blocking the distractor in position, while stabilizers 14a-b abut against the spine, seeking a better position for body 10.

A portion 23 of rod 20 close to end 22 (FIG. 2B) has a threaded portion 23 on which a nut 25 (FIG. 2G) of the distractor can be screwed. This nut 25 has a through hole 27a, and a cam-shaped surface 26, adapted to engage with the cam surfaces 17c-d of stabilizers 14c-d, causing a rotation thereof.

Figure 2D:
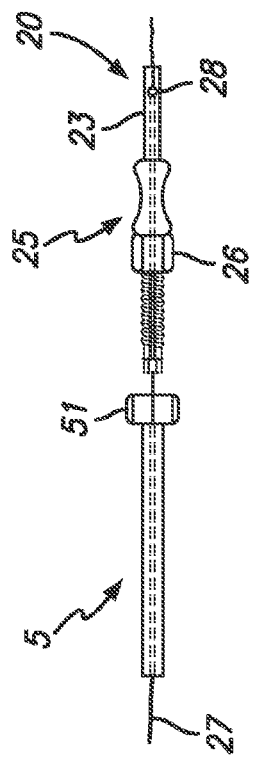
FIG. 2D shows means operated percutaneously for adjusting the position of the stabilizers of the second couple, comprising a cam-shaped nut adapted to be screwed on a screw threaded portion of the rod and one tool adapted to engage this nut, as well as guiding means to wire and for tool.

Nut 25 is maneuvered by a tool 5 that has an hexagonal female head 51 adapted to engage with cam-shaped nut 25 (FIGS. 2D and 2E).

By this maneuver, the nut 25 moves to the position shown in FIG. 2E and stabilizers 14c-d rotate running from the closed position of FIG. 2C to the spread apart position of FIG. 2E.

In FIG. 2D, a guiding wire 27 is visible, for example a Kirschner or K wire, passing in rod 20 through end 22 and recess 29 (FIG. 2F). When arranging the distractor in the interspinous gap, the wire 27 extends rigidly in the patient, thus allowing the introduction in a first phase of tool 4 and in a second phase of tool 5. In this way, tools 4 and 5 can be guided towards distraction body 1 to the interspinous position. To allow the movement of the wire 27, the tools 4 and 5 have recesses 42 and 52 (FIGS. 2C and 2E). Obviously, the introduction can be made also without guiding means 27.

In the various exemplary embodiments of the distractor as described in the present application, stabilizers 14a-d are advantageously made of titanium and the central body 10 has a core 8 of titanium and a coating surface 3, for example made of polyetheretherketone (PEEK®); this is shown in the median cross sectional view of FIG. 2F, according to plane F-F whose shape is shown in FIG. 2E; in this cross-section, central recess 15 and rod 20 with recess 29 are also shown. Alternatively, the coating surface 3 can be made of a soft material, for example polyurethane foam, according to the disc degeneration degree of the patient.

Figure 4C:
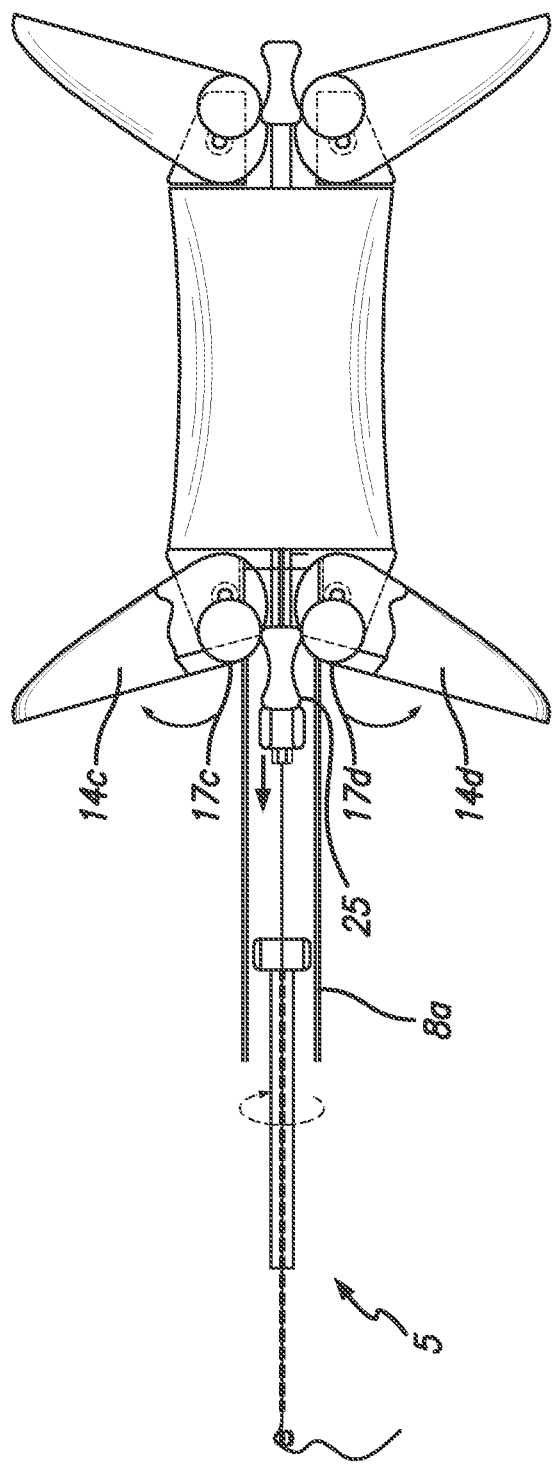

In FIGS. 3A-3C it is shown in more detail how the device 200 as described can be guided towards the interspinous gap 69 set between the spinous apophysis 67 and 68 of two adjacent vertebrae, by means of a Kirschner wire 27. To this end, as already said above, rod 20 (FIG. 2B) is open axially. Furthermore, in order to place the distractor in the interspinous gap, a tubular guide 8a can be provided, as shown in detail in FIG. 4A. The guide has, at one end thereof, a couple of gripping teeth 81 adapted to engage with conjugate holes 82 arranged within the longitudinal recess 16 of stabilizers 14c and 14d. The tubular guide has an inner recess such that it allows the movement of the tools 4 and 5 of FIGS. 2C and 2E, as shown respectively in FIGS. 4B and 4C, for opening the couples of stabilizers, 14a-b and 14c-d respectively.

FIGS. 5A-D show again the interspinous distractor 100 of FIG. 1A, where the means which can be operated percutaneously for adjusting the position of stabilizers 14a-b and 14c-d comprises flexible tie members or wires 6 and 7. In particular, flexible tie member 6 has two ends 61a and 61b fixed to stabilizers 14a-b, in this case through two hinges 13. A rod 19 is also provided, guiding two branches of flexible tie member 6 towards the two stabilizers 14a-b. Flexible tie member 6 comes out from distractor 1 running through the longitudinal recess 15 of elongated body 10 and through recess 16 determined between the two stabilizers 14c-d. An end 62 of flexible tie member 6, opposite to ends 61a-b, remains out of the body of the patient.

In the same way, a flexible tie member 7 has two ends 71c-d fixed to stabilizers 14c-d by two hinges 13 and a rod 19. This flexible tie member comes out of distractor 1, running also through the recess 16. An end 72, opposite to ends 71c-d remains out of the body of the patient. A traction on the flexible tie members 6 and 7, effected from an endoscopic position, allows bringing respectively stabilizers 14a-b and 14c-d from the closed position shown in FIG. 5A to the spread apart position shown in FIG. 5D.

Once the stabilizers of the two couples are brought to the respective spread apart positions, the two flexible tie members 6 and 7 act as guiding means for a device 30 for blocking the stabilizers in the spread apart position; this device has a couple of friction counter rotating wheels 31, and a tool 9 is used, comprising a recess 91 and a head 92 adapted to arrange the device 30 to a contrast with support 33. Traction on wires 6 and 7 forces the device 30 in this position, due to the friction exerted with and between friction wheels 31.

Alternatively, or in addition to the friction wheels, circular sectors can be provided opposite to each other and in geared fashion, kept in blocked position with the locked wires within them. As a further alternative, or in addition, the wires can be locked with rings of a metal material, for example titanium, sliding along the wire and then locked on the wire with plastic deformation, in order to prevent a back sliding of the wire.

Figure 5E:
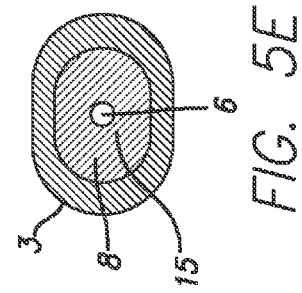
FIG. 5E shows the median cross sectional view E-E of the elongated body of the distractor shown in FIG. 5D.
Figure 5C:
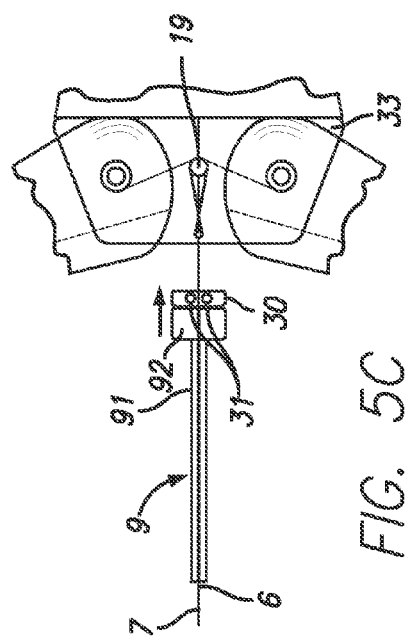
FIG. 5C shows a wire pulling member, consisting of a couple of friction wheels.
Figure 5D:
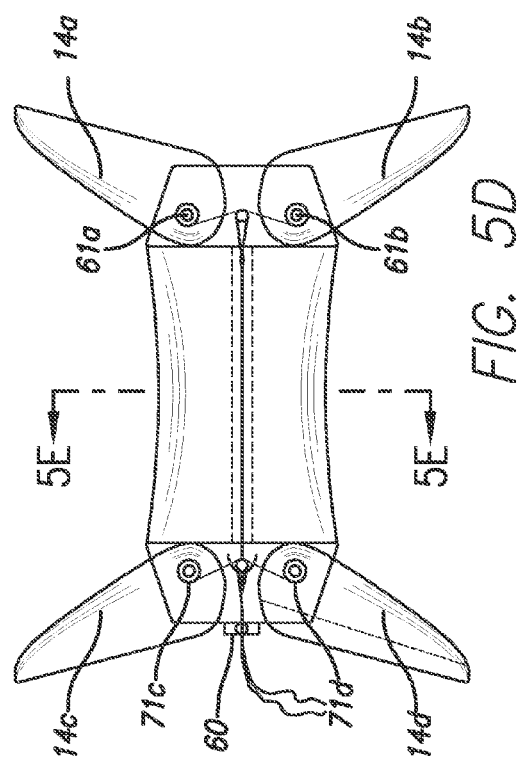
FIG. 5D shows the distractor of FIG. 5B after opening also of the stabilizers of the second couple by means of traction of a second flexible tie member, the two flexible tie members being pulled by the member of FIG. 5C.

Also in this case, the central body and the stabilizers have a core of titanium, with a coating surface 3 of polyetheretherketone (PEEK®), as shown in FIG. 5E, which is a cross sectional view of elongated body 10 according to plane E-E, whose shape is indicated in FIG. 5D, where central recess 15 and flexible tie member 6 are also shown.

Similarly, the operation of distractor 600 shown in FIGS. 6A-D provides the same concepts. This distractor differs from distractor 100 of FIGS. 5A-D, since stabilizers 14b and 14d, which are arranged in use below the median horizontal plane of body 10 of the distractor, are shorter than the corresponding stabilizers 14a and 14c, as shown, in particular, in FIGS. 6A and 6B. This arrangement is used to avoid interference with the spinous processes or lateral processes of the vertebra just below the two distracted vertebrae, which can occur, in particular, when there are vertebral degenerations or in case of scoliosis. Furthermore, device 600 has stabilizers 64a-d that are asymmetrical with respect to a desired vertical plane; such stabilizers can be conceptually obtained cross-sectioning corresponding stabilizers of the type 14a-d, symmetrical, with a vertical plane parallel to the axis of the distractor, and removing one of the two parts of each lateral stabilizer thus obtained, typically the part having smaller size. This is used in order to avoid an interference with the lateral processes, as shown in FIG. 7.

Figure 6E:
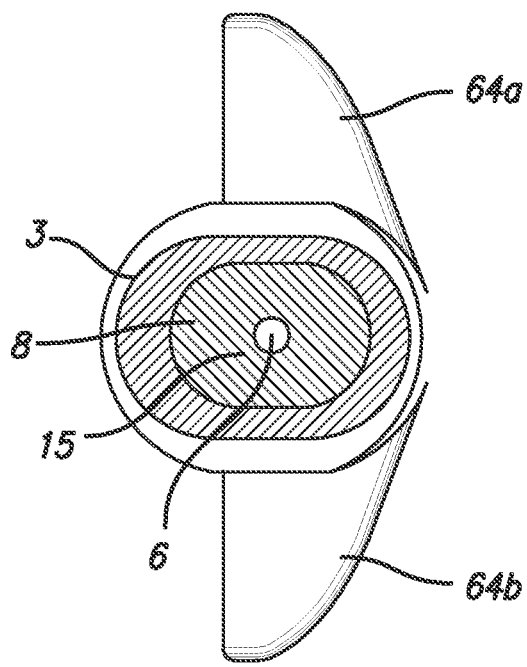
FIG. 6E shows the median cross sectional view E-E of a distractor according to the exemplary embodiment of the distractor of FIG. 6A, where the stabilizers are also asymmetrical, and arranged asymmetrically with respect to the diametrical vertical plane of the body of the distractor.
Figure 6F:
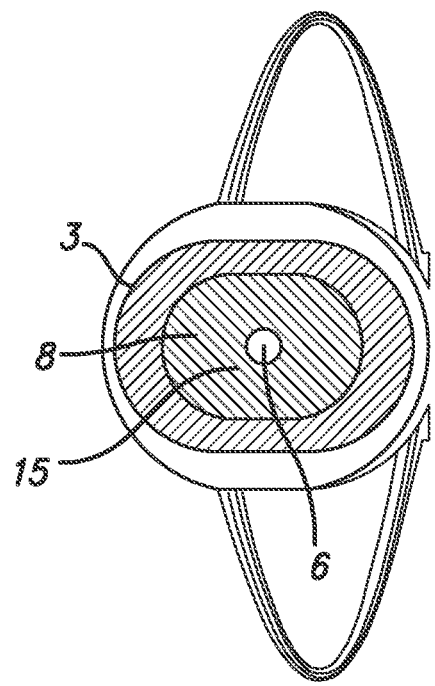
FIG. 6F shows the median cross sectional view E-E of a distractor according to the exemplary embodiment of the distractor of FIG. 6A, wherein the stabilizers are also symmetrical with respect to a longitudinal median plane, and are arranged asymmetrically with respect to the diametrical vertical plane of the body of the distractor.

Alternatively to what shown in FIG. 6D, FIG. 6E represents a solution with stabilizers that are symmetrical with respect to their own longitudinal median plane, but arranged asymmetrically with respect to the vertical median plane of the body of the distractor.

Figure 1C:
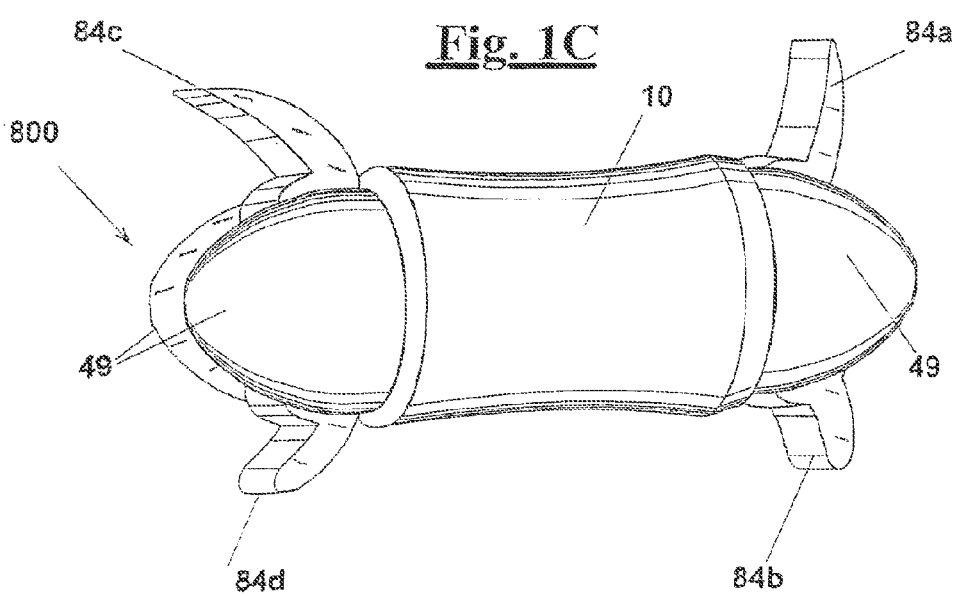
FIG. 1C is a perspective view of a second embodiment of an interspinous distractor according to the invention, where the stabilizers of both couples of stabilizers are in open position.

The distractor 800 shown in FIGS. 8A-E, as well as in FIG. 1C, has the two couples of stabilizers 84a-b and 84c-d enclosed between fixed protection shells 49. The opening/closing movement of the stabilizers is performed by translating a rod 70 (FIG. 8B) with a cam-shaped end 77, and a nut 75 with a cam-shaped surface 76 (FIG. 8D), the translation being operated by a tool in a similar way as described for distractor 200 of FIGS. 2A-G.

In this device, an anatomic solution is used that provides lower stabilizers 84b and 84d of length lower than the higher stabilizers 84a and 84c. Like in the exemplary embodiments previously described, the concave part of the stabilizers of the couple 84a-b is oriented, in open position, opposite to the central body 10, the stabilizers of this couple being adapted to rotate from the closed position of FIG. 8A to the spread apart position of FIGS. 5C and 8D, and eventually to the closed position shown in FIG. 8G. This is used to assist a percutaneous extraction of the distractor from the interspinous gap, the extraction occurring according to the direction 89 of the arrow shown in FIG. 8G.

Concerning the stabilizers of the couple 84c-d, their convex part is oriented, in the spread apart position, opposite to the central body. Furthermore, stabilizers 84c-d are capable of rotating about the pivot point 83 beyond the spread apart position continuing further for angles larger than 90°, in particular, between 120° and 180°, and in FIG. 8G of about 150°. As shown in FIG. 8G, the two stabilizers 84c-d have a curved shape with concavity such that, during the introduction according to arrow 88 (FIG. 8A), it is oriented opposite to the axis 1 of the body and, during the extraction according to arrow 89 (FIG. 8G), it is oriented according to the same side of the axis 1 of the body.

Figure 8A:
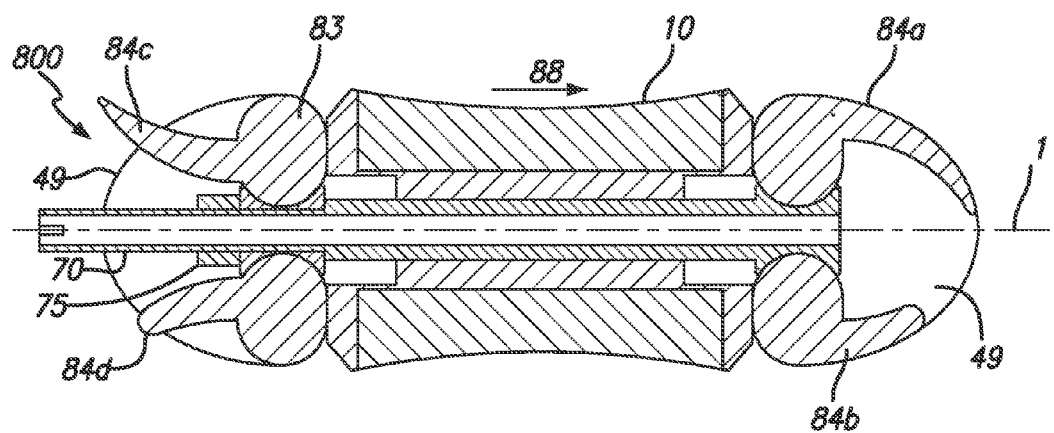
FIG. 8A is a cross sectional view of an interspinous distractor according to the invention, where the position of the stabilizers is changed by means of cam-shaped elements adapted to be housed in a space between the stabilizers.
Figure 8C:
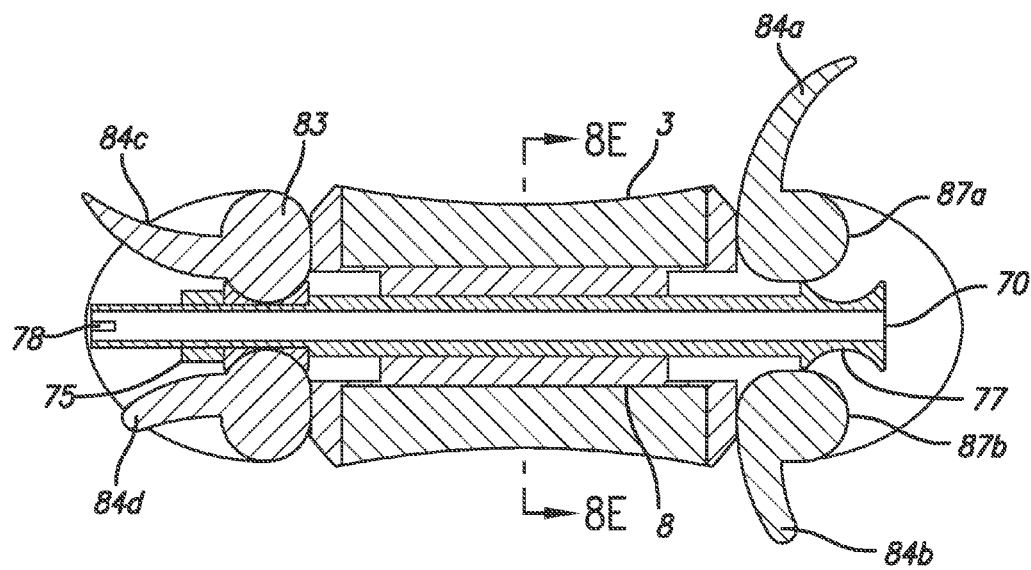
FIG. 8C shows the distractor of FIG. 8A after variation of the position of the stabilizers of the first couple by means of a tool similar to that shown in FIG. 2B.
Figure 8B:
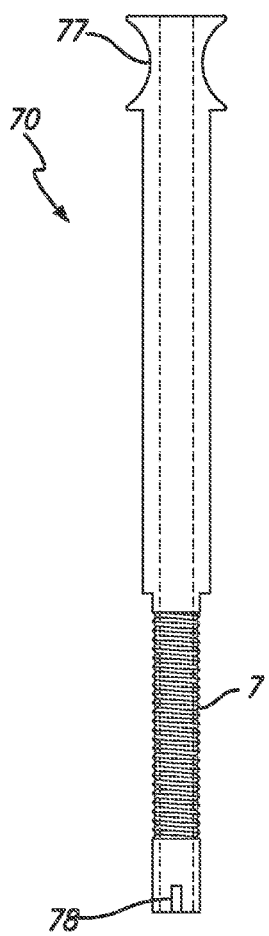
FIG. 8D shows a cam-shaped nut for adjusting the position of the stabilizers of the second couple, the nut being adapted to be screwed on a screw threaded portion of the rod shown in FIG. 2B and to be maneuvered by a tool shown in FIG. 2D and in FIG. 10.
FIG. 8E shows the distractor of FIG. 2A after variation of the position of the stabilizers of the second couple by means of the nut and the tool.
FIG. 8F shows a median cross sectional view F-F of the elongated body of the distractor shown in FIG. 8E.
FIG. 8G shows the distractor of FIG. 8 A-C-E where the position of the stabilizers of the second couple has been changed in a backward position to assist percutaneous extraction.
Figure 8D:
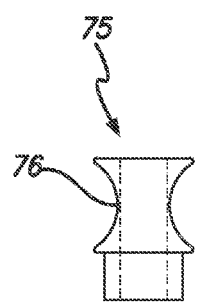
Figure 8F:
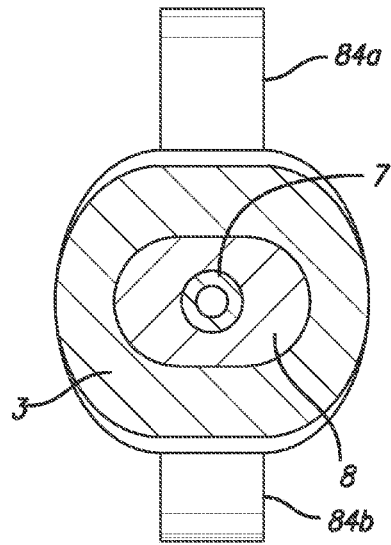
Figure 8E:
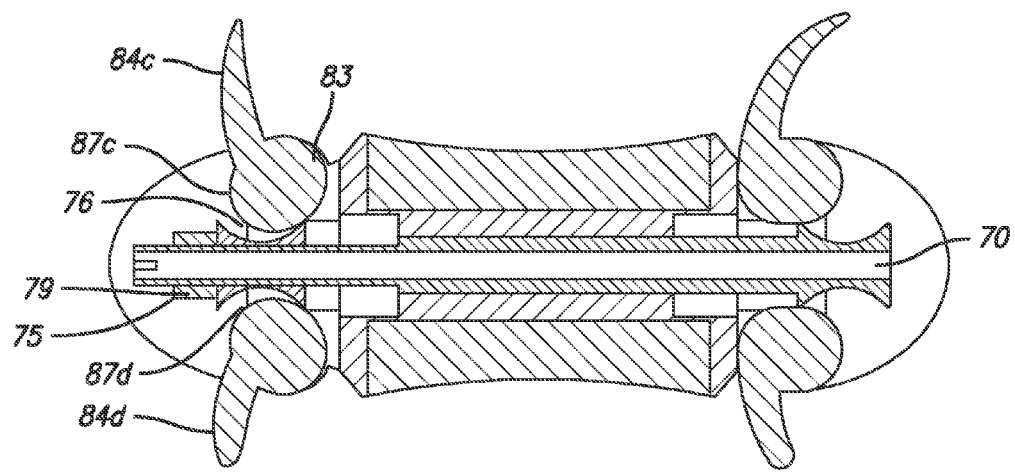
Figure 8G:
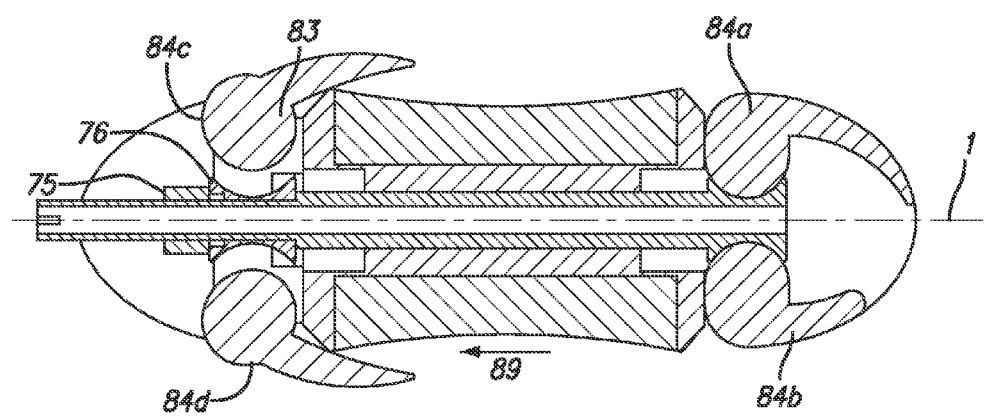

The stabilizers of such couple 84*c*-*d* can then rotate from the closed position of FIG. 8A to the spread apart position of FIGS. 5C and 5D, up to reaching the closed position shown in FIG. 8G. In the latter closed position, stabilizers 84*c*-*d* have a rotation induced by the same extraction, once the cams 84*c* and 84*d* have abandoned the cam-shaped portion 76 of the cam-shaped nut 75. In particular, the opposite concavity of stabilizers 84*c*-*d* is used to assist the percutaneous extraction of the distractor from the interspinous gap according to the direction 89. With a numbering similar to that relative to distractor 200, the other elements of the distractor 800 are described in FIGS. 8A-8G.

As shown in FIG. 9, in order to adjust the opening angle of a distal couple of stabilizers 84*c*-*d* by rod 70, a tool 90 can be used, having a couple of symmetrical tools 96 engageable with two horizontal pins 99 integral to a fixed portion of the distractor 800, for example with protective shells 49, such tools being adapted to block nut 75 in a determined position; tool 90 comprises, furthermore, a rotatable device 94 with an hexagonal female head adapted to engage with the male head of rod 70; with a rotation of the tool it is therefore possible to move rod 70, causing a translation associated with the rotation, suitable for moving stabilizers 84*c*-*d* with micrometric precision and according to reproducible positions.

With reference to FIG. 10, the proximal end of stabilizers 84*c* and 84*d* have a convex shape, which can be a cam-like shape 87*c* and 87*d*, whereas the cam-shaped portion 76 of the rod has a corresponding concave shape, whereby the convex and concave shapes form two conjugate profiles. This allows a micrometric adjustment of stabilizers 84*c* and 84*d*.

Figure 11:
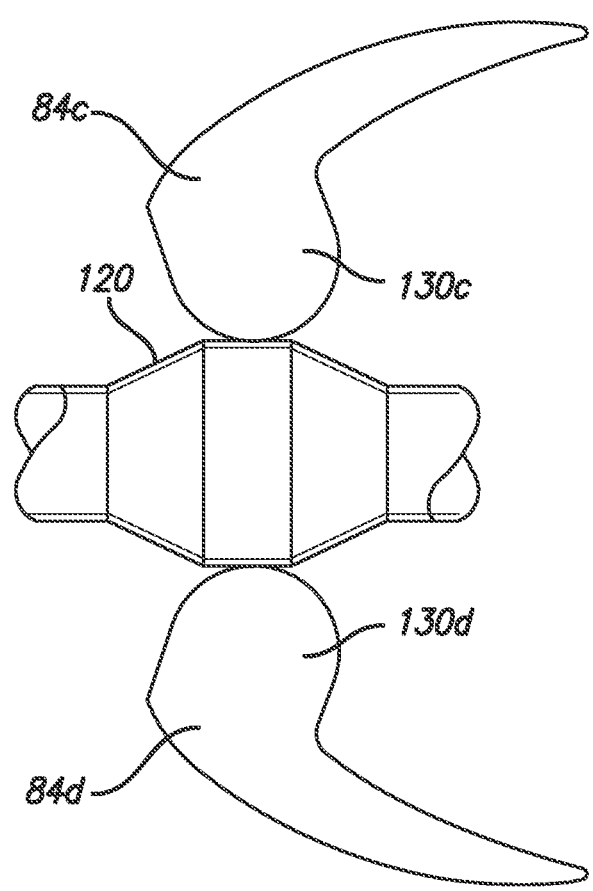
FIG. 11 shows a detail of an alternative conjugate profile adapted to provide the rotation of two stabilizers of the distractor of FIGS. 8A-G.

An alternative exemplary embodiment that can be applied to any embodiments of the invention is shown in FIG. 11, providing conjugate profiles 130*c*-*d* of the proximal end and of the cam-shaped portion 120 of the rod that are convex, and may have gear-like portions on the surface (not shown).

Figure 12:
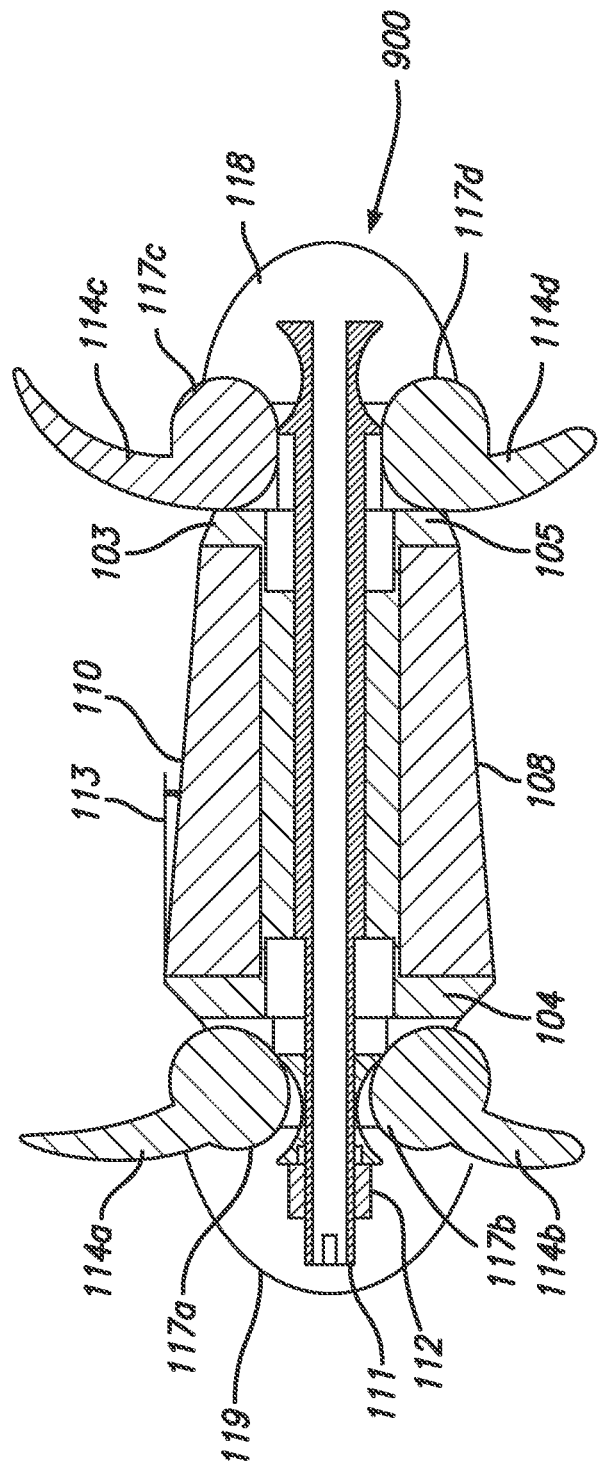
FIG. 12 is a cross sectional view of a distractor having a different shape of the central body, and stabilizers that can be operated with mechanisms similar to the distractor of FIGS. 8A-G.

FIG. 12 shows, according to another exemplary embodiment of the invention, a distractor 900 having central body 110 with the shape of a right circular frustum of cone, with the generatrix at an angle 113 of 5° with respect to the axis. Like the central body 10 of the device 800 of FIGS. 8A-G, the central body 110 has a coating 108 of a material chosen according to the disc degeneration degree of the patient, and an inner core 103 of titanium. To provide the frustum-conic shape of the central body 110, the core 108 has an end 104 having size larger than the end 105, as well as stabilizers 114*a/b* larger than stabilizers 114*c/d*. The distractor 900 can be used advantageously for patients suffering from scoliosis. In this case, the part of stabilizer corresponding to end 104 is placed according to the part of the spine that has a concavity. In analogy to distractor 800, distractor 900 has its lower stabilizers 114*b* and 114*d* having a length lower than the higher stabilizers of a same couple, respectively 114*a* and 114*c*, and this is an anatomic solution that makes the distractor 900 also suitable for treating patients suffering from scoliosis. The position of stabilizers 114*a*-*d* is adjusted acting on movable components of the distractor 900 similar to those of the distractor 800, in particular, stabilizers 114*a* and 114*d* are brought from a closed position to a spread apart position and vice-versa by translating a rod 111 similar to rod 70 of FIG. 8B, whereas stabilizers 114*b* and 114*c* are moved by nut 112 similar to nut 75 of FIG. 8D, owing to the cam surfaces of the rod and of the nut adapted to engage, respectively, the couples of cam surfaces of stabilizers 114*a*-*d* and 114*c*-*d*.

Obviously, the solution of FIG. 12 can be applied to any desired type of interspinous distractor.

The foregoing description of a specific embodiment will so fully reveal the invention according to the conceptual point of view, so that others, by applying current knowledge, will be able to modify and/or adapt for various applications such an embodiment without further research and without parting from the invention, and it is therefore to be understood that such adaptations and modifications will have to be considered as equivalent to the specific embodiment. The means and the materials to realise the different functions described herein could have a different nature without, for this reason, departing from the field of the invention. It is to be understood that the phraseology or terminology employed herein is for the purpose of description and not of limitation.

The invention claimed is:

1. An interspinous intervertebral distractor capable of introduction into and extraction from the human body and comprising:

an elongated body with a first and a second end, said elongated body having a longitudinal axis with the first end on one side of the elongated body and the second end on a longitudinally opposite side of the elongated body with respect to the first end, and a transversal dimension perpendicular to the longitudinal axis;

four mobile stabilizers having a curved shape and connected to the elongated body, a first pair of mobile stabilizers of the four mobile stabilizers being connected to the first end of the elongated body and a second pair of mobile stabilizers being connected to the second end of the elongated body, each of the four mobile stabilizers connected at a respective individual pivot point of the elongated body distant from the longitudinal axis, wherein the curved shape of the four mobile stabilizers exhibits a rounded side adjacent to the elongated body, a first lateral side and a second lateral side, the first lateral side being substantially convex and the second lateral side being substantially concave, and wherein the first lateral side and the second lateral side converge to a common point; and a moveable element, coupled with the respective pivot points of the four mobile stabilizers of the elongated body and configured to be moved along the longitudinal axis of the elongated body to cause rotation of one or both pairs of the mobile stabilizers around the respective pivot points of said stabilizers, wherein:

at least one pair of said mobile stabilizers is rotatable about said respective pivot points beyond a spread apart position and each mobile stabilizer of said pair is rotatable for angles larger than 90° with respect to a closed position, in particular, between 120° and 180°, and the mobile stabilizers of said first and second pair of mobile stabilizers and the moveable element are configured so that the second pair of mobile stabilizers have an introduction orientation wherein the rounded side of each mobile stabilizer is located upstream from the lateral sides relative to the target surgical site during the introduction of the interspinous intervertebral distractor into the body, and an extraction orientation, same as the introduction orientation, wherein the rounded side of each mobile stabilizer is located upstream from the lateral sides relative to the target surgical site during extraction of the interspinous intervertebral distractor from the body, and the first pair of mobile stabilizers have an introduction orientation wherein the rounded side of each mobile stabilizer is located downstream from the lateral sides relative to the target surgical site during introduction of the interspinous intervertebral distractor into the body, and an extraction orientation, opposite to the introduction orientation, wherein the rounded side of each mobile stabilizer is located upstream from the lateral sides relative to the target surgical site during extraction from the body.

2. The intervertebral distractor according to claim 1, wherein the rotation of the mobile stabilizers around the respective pivot points is continuous.

3. The intervertebral distractor according to claim 1, wherein said movable element causes, in an introduction direction, opening at different times of the first pair and the second pair of mobile stabilizers.

4. The intervertebral distractor according to claim 1, wherein said elongated body has substantially elliptical transversal sections, wherein, during an operative condition of said distractor, a longer axis of the transversal sections lies in a plane substantially orthogonal to the spine.

5. The intervertebral distractor according to claim 1, wherein said elongated body is a frustoconically shaped body, in particular, with a cone angle of the frustoconically shaped body of 4° to 5°.

6. The intervertebral distractor according to claim 1, wherein the first and second pair of mobile stabilizers comprise a first lateral stabilizer and a second lateral stabilizer arranged, during an operative condition of said distractor, below a median horizontal plane of the body of the distractor, and a corresponding third lateral stabilizer and a fourth lateral stabilizer arranged, during an operative condition of said distractor, above the median horizontal plane, wherein the first lateral stabilizer and the second lateral stabilizer are shorter than the corresponding third lateral stabilizer and fourth lateral stabilizer.

7. The intervertebral distractor according to claim 1, wherein said mobile stabilizers are asymmetrical in a vertical plane.

8. The intervertebral distractor according to claim 1, wherein said mobile stabilizers are enclosed laterally between fixed protection shells, said shells having a pointed profile such that resistance is reduced during percutaneous introduction or extraction.

9. The intervertebral distractor according to claim 1, wherein said movable means that can be operated percutaneously comprises:
a flexible tie member fixed to at least one pair of the first and second pair of mobile stabilizers, such that the mobile stabilizers fixed to the flexible tie member are brought from the closed position to the spread apart position by pulling the flexible tie member, and
blocking means for blocking the flexible tie member when the mobile stabilizers fixed to the flexible tie member have achieved the spread apart position.

10. The interspinous intervertebral distractor according to claim 1, wherein:
the first and second pair of mobile stabilizers are adapted to rotate from a closed position, in which they form a pointed extension of said elongated body, assisting a percutaneous implantation of said distractor, to a spread apart position, where said mobile stabilizers, during an operative condition of said distractor, limit the movement of said distractor, providing a barrier adapted to contain between them said spinous processes;
and wherein the movable element can be operated percutaneously, said movable element being movable along the longitudinal axis of the elongated body and associated with said elongated body and said mobile stabilizers, for bringing said mobile stabilizers from said closed position to said spread apart position or vice versa,
said mobile stabilizers being connected to said ends of said body at individual pivot points distant from said axis, said mobile stabilizers having with respect to said body a distal end and a proximal end, such that said movable means act on said mobile stabilizers, for causing both said first and said second pair of mobile stabilizers to rotate about said pivot points, such that said distal end moves from said closed position to said spread apart position and said proximal end is maintained close to said axis,
wherein the said movable element that can be operated percutaneously comprises:
a flexible tie member fixed to the mobile stabilizers of at least one pair of said first and second pair of mobile stabilizers, such that such mobile stabilizers fixed to the flexible tie member are brought from the closed position to the spread apart position by pulling the tie flexible member, and
blocking means for blocking the flexible tie member when the mobile stabilizers fixed to the flexible tie member have achieved the spread apart position, and
wherein said blocking means for blocking the flexible tie member comprises a pair of counter rotating friction wheels or circular sectors arranged about respective axes substantially perpendicular to a direction defined by the flexible tie member when stretched, said wheels or circular sectors being such that said wheels or circular sectors keep an interference position due to a mutual friction exerted, wherein the flexible tie member is arranged between said wheels or circular sectors.

11. The interspinous intervertebral distractor according to claim 1, wherein
the first pair of mobile stabilizers have an extraction orientation wherein the mobile stabilizers are rotated between 120° and 180° with respect to the introduction orientation.

12. An interspinous intervertebral distractor comprising:
an elongated body with a first and a second end, said elongated body having a longitudinal axis with the first end on one side of the elongated body and the second end on a longitudinally opposite side of the elongated body with respect to the first end, and a transversal dimension perpendicular to the longitudinal axis, adapted to provide an interspinous support between two adjacent spinous processes;
four mobile stabilizers having a curved shape and connected to the elongated body, a first pair of mobile stabilizers of the four mobile stabilizers being connected to the first end of the elongated body and as a second pair of mobile stabilizers being connected to the second end of the elongated body, each of the four mobile stabilizers connected at a respective individual pivot point of the elongated body distant from the longitudinal axis, wherein the curved shape of the four mobile stabilizers exhibits a rounded side adjacent to the elongated body, a first lateral side and a second lateral side, the first lateral side being substantially convex and the second lateral side being substantially concave, wherein the first lateral side and the second lateral side converge to a common point, wherein the mobile stabilizers of said first pair of mobile stabilizers have a cam-shaped surface made up by said rounded side adjacent to the elongated body;

a rod configured to be slidingly moved in a recess along the longitudinal axis of the elongated body; and a cam-shaped portion located at an end of the rod, the cam-shaped portion having a curved shape and being configured to transform a sliding movement of the rod in the recess into a rotational movement of the mobile stabilizers of said first pair around the respective pivot points from a closed position being substantially aligned to the longitudinal axis of the elongated body to a spread apart position and vice versa, wherein the cam-shaped surface of the mobile stabilizers is a shape corresponding to the curved shape of the cam-shaped portion and engaging with the curved shape of the cam-shaped portion.

13. The intervertebral distractor according to claim 12, comprising:

a cam-shaped element configured to be housed in a space comprised within the second pair of mobile stabilizers and to be maneuvered with a second tool, the cam-shaped element being engageable and lockable on a portion of the rod opposite to the cam-shaped portion, in order to cause a rotation of the second pair of mobile stabilizers from the closed position to the spread apart position.

14. The intervertebral distractor according to claim 13, wherein said portion of the rod opposite to the cam-shaped portion has a threaded portion and the cam-shaped element is a cam-shaped nut adapted to be screwed on said threaded portion to cause a rotation of the second pair of mobile stabilizers from the closed position to the spread apart position or vice versa.

15. The intervertebral distractor according to claim 12, wherein said rounded side adjacent to the elongated body has a convex shape, and said cam-shaped portion has a corresponding concave shape, whereby said convex shape and concave shape form two conjugate profiles.

16. The intervertebral distractor according to claim 12, wherein said rod has a gripping end opposite to the cam-shaped portion, and said gripping end is adapted to be percutaneously maneuvered with a first tool.

17. The intervertebral distractor according to claim 12, wherein said intervertebral distractor further comprises guiding means for guiding the cam-shaped portion and a tool towards the distraction body arranged in an intervertebral interspinous gap.

18. The intervertebral distractor according to claim 12, further comprising a tubular guide having at the end means for releasably engaging the intervertebral distractor.

19. An interspinous intervertebral distractor capable of introduction into and extraction from the human body and comprising:

an elongated body with a first and a second end, said elongated body having a longitudinal axis with the first end on one side of the elongated body and the second end on a longitudinally opposite side of the elongated body with respect to the first end, and a transversal dimension perpendicular to the longitudinal axis;

four mobile stabilizers having a curved shape and connected to the elongated body, a first pair of mobile stabilizers of the four mobile stabilizers being connected to the first end of the elongated body and a second pair of mobile stabilizers being connected to the second end of the elongated body, each of the four mobile stabilizers connected at a respective individual pivot point of the elongated body distant from the longitudinal axis, wherein the curved shape of the four mobile stabilizers exhibits a rounded side adjacent to the elongated body, a first lateral side and a second lateral side, the first lateral side being substantially convex and the second lateral side being substantially concave, and wherein the first lateral side and the second lateral side converge to a common point; and a moveable element, coupled with the respective pivot points of the four mobile stabilizers of the elongated body and configured to be moved along the longitudinal axis of the elongated body to cause rotation of one or both pairs of the mobile stabilizers around the respective pivot points of said stabilizers, wherein:

at least one pair of said mobile stabilizers is rotatable about said respective pivot points beyond a spread apart position and each mobile stabilizer of said pair is rotatable for angles larger than 90° with respect to a closed position, in particular, between 120° and 180°, and the mobile stabilizers of said first pair of mobile stabilizers and the moveable element are configured so that:

the first pair of mobile stabilizers have an introduction orientation wherein said first lateral substantially convex side of each mobile stabilizer faces said elongated body, and the first pair of mobile stabilizers have an extraction orientation wherein said second lateral substantially concave side of each mobile stabilizer faces said elongated body.

\* \* \* \* \*